US010077293B2

(12) United States Patent
Seo et al.

(10) Patent No.: US 10,077,293 B2
(45) Date of Patent: Sep. 18, 2018

(54) **ANTIMICROBIAL PEPTIDE ANALOGUES DERIVED FROM ABALONE (*HALIOTIS DISCUS*) AND ANTIMICROBIAL PHARMACEUTICAL COMPOSITION CONTAINING THE SAME**

(71) Applicant: INDUSTRY-ACADEMIC COOPERATION FOUNDATION, KUNSAN NATIONAL UNIVERSITY, Jeollabuk-do (KR)

(72) Inventors: Jung-Kil Seo, Jeollabuk-do (KR); Ki-Young Lee, Jeollabuk-do (KR); Sang-man Cho, Jeollabuk-do (KR); In-Ah Lee, Jeollabuk-do (KR)

(73) Assignee: INDUSTRY-ACADEMIC COOPERATION FOUNDATION, KUNSAN NATIONAL UNIVERSITY, Jeollabuk-Do (KR)

( * ) Notice: Subject to any disclaimer, the term of this patent is extended or adjusted under 35 U.S.C. 154(b) by 0 days.

(21) Appl. No.: 15/364,398

(22) Filed: Nov. 30, 2016

(65) Prior Publication Data
US 2018/0141984 A1 May 24, 2018

(30) Foreign Application Priority Data

Nov. 18, 2016 (KR) .................. 10-2016-0154215

(51) Int. Cl.
| | |
|---|---|
| *C07K 7/04* | (2006.01) |
| *A61K 38/04* | (2006.01) |
| *A61Q 17/00* | (2006.01) |
| *A61Q 19/00* | (2006.01) |
| *A61Q 19/10* | (2006.01) |
| *C07K 14/435* | (2006.01) |
| *A61K 8/64* | (2006.01) |
| *A61K 8/04* | (2006.01) |
| *A23K 20/147* | (2016.01) |
| *A23L 33/18* | (2016.01) |
| *A61K 38/00* | (2006.01) |

(52) U.S. Cl.
CPC ...... *C07K 14/43504* (2013.01); *A23K 20/147* (2016.05); *A23L 33/18* (2016.08); *A61K 8/046* (2013.01); *A61K 8/64* (2013.01); *A61Q 17/005* (2013.01); *A61Q 19/007* (2013.01); *A61Q 19/10* (2013.01); *A23V 2002/00* (2013.01); *A61K 38/00* (2013.01)

(58) Field of Classification Search
CPC .... C07K 14/43504; A61K 8/64; A61K 8/046; A61K 38/00; A61Q 17/005; A61Q 19/007; A61Q 19/10; A23K 20/147; A23L 33/18; A23V 2002/00
See application file for complete search history.

(56) References Cited

U.S. PATENT DOCUMENTS

2004/0053847 A1* 3/2004 Shai ............... A23L 3/3526
514/2.4
2006/0062758 A1* 3/2006 Cui ................. A61K 9/0043
424/85.1

FOREIGN PATENT DOCUMENTS

| KR | 101384578 | 4/2014 |
|---|---|---|
| KR | 1014222710000 | 7/2014 |

OTHER PUBLICATIONS

Search Result for SEQ ID No. 6, from http://score.uspto.gov/ ... 64398&seqId=09323b6782815e72&ItemName=20170901_165928_us-15-364-398a-6.rup&ItemType=4&startByte=0, pp. 1-119, Sep. 1, 2017.*
Torri et al, A DNA Polymerase beta in the Mitochondrion of the Trypanosomatid Crithidia fasciculata, The Journal of Biological Chemistry, 1995, 270, pp. 3495-3597.*
Water, from http://www.biology-online.org/dictionary/Water, pp. 1-3, accessed Apr. 24, 2014.*
Kim et al, Disperse Distribution of Cationic Amino Acids on Hydrophilic Surface of Helical Wheel Enhances Antimicrobial Peptide Activity, Biotechnol. Bioeng., 2010, 107, pp. 216-223.*
Wierzbicki et al, Structure-Function Relationship in the Antifreeze Activity of Synthetic Alanine-Lysine Antifreeze Polypeptides, Biomacromolecules, 2000, 1, pp. 268-274.*
Infectious diseases, from http://www.mayoclinic.org/diseases-conditions/infectious-diseases/symptoms-causes/dxc-2 . . . , pages 1-2, accessed Sep. 5, 2017.*
Nordqvist, Infection: Types, causes, and differences, from http://www.medicalnewstoday.com/articles/196271.php, Aug. 22, 2017, pp. 1-19.*
Papo et al, The Consequence of Sequence Alteration of an Amphipathic alpha-Helical Antimicrobial Peptide and its Diastereomers, J. Biol. Chem., 2002, 277, pp. 33913-33921.*
Leucidal Liquid, from ActiveMicro Technologies, Sep. 11, 2014, pp. 1-3.*

* cited by examiner

*Primary Examiner* — Julie Ha
*Assistant Examiner* — Li N Komatsu
(74) *Attorney, Agent, or Firm* — Duane Morris LLP; Gregory M. Lefkowitz; Jason M. Nolan

(57) ABSTRACT

The present disclosure relates to an antimicrobial peptide analog derived from abalone and an antimicrobial pharmaceutical composition containing the same. The antimicrobial peptide analog according to the present disclosure is designed based on hdMolluscidin which is a peptide derived from the gill of abalone and has been designed to be commercially viable by reducing the number of amino acids. Despite the reduced number of amino acids, the designed peptide analog exhibits very superior antimicrobial activity as well as high membrane permeability and low hemolytic activity.

13 Claims, 10 Drawing Sheets
Specification includes a Sequence Listing.

Fig. 1

```
                    10         20         30
                    |          |          |
hdMolluscidin  AATKPKK----AGAEAAPKNPAKKQTKKKP
cgMolluscidin  AAT-AKKGAKKADAPAKPKKATKPKSPKKA 40         50
                    |          |
hdMolluscidin  AKKAGGKKKPKRAGAKK-AKK------
cgMolluscidin  AKKAGAKKGVKRAG-KKGAKKTTKAKK
```

Fig. 2

```
         10        20        30        40
         |         |         |         |
    AATKPKKAGAEAAPKKPAKKQTKKKPAKKAGGKKKPKRAGAKKAKK
    cccccccchhhhhccchhhhhhcchhhhhccccchhhhcccceec
        Fragment 1        Fragment 2
```

(h: α-helix, e: β-sheet, c: random coil)

Ab2-5

Ab4-7

Piscidin1

ANTIMICROBIAL PEPTIDE ANALOGUES DERIVED FROM ABALONE (*HALIOTIS DISCUS*) AND ANTIMICROBIAL PHARMACEUTICAL COMPOSITION CONTAINING THE SAME

CROSS-REFERENCE TO RELATED APPLICATIONS

This application claims priority under 35 U.S.C. § 119 to Korean Patent Application No. 10-2016-0154215 filed on Nov. 18, 2016 in the Korean Intellectual Property Office, the disclosure of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Dec. 21, 2016, is named G1035-09601_SL.txt and is 4,142 bytes in size.

TECHNICAL FIELD

The present disclosure relates to an antimicrobial peptide analogue derived from abalone (*Haliotis discus*) and an antimicrobial pharmaceutical composition containing the same.

BACKGROUND hdMolluscidin is an antimicrobial peptide consisting of 46 amino acids with a molecular weight of 4767.2 Da, purified from the gill of abalone (*Haliotis discus*). It is an antimicrobial peptide which exhibits little hemolytic activity and exhibits strong antimicrobial activity against Gram positive and Gram negative bacteria but no activity against *C. albicans*. In order to overcome the limited activity of hdMolluscidin and the limitation caused by the length of 46 amino acids, it is necessary to design and develop a new antimicrobial peptide such as an analogue with a fragmented length and increased antimicrobial activity.

According to recent studies, it is reported that the antimicrobial peptide plays an important role as one of effective defense mechanisms against external sources of infection in the gill and mantle of oyster and sea mussel. This result suggests that the gill and mantle are organs which play an important role in the immune mechanism of shellfish, as a primary defense against external environments, and they are important targets in the search and purification of substances having antimicrobial activity. However, there has not been much effort in developing novel antimicrobial peptides therefrom.

Korean Patent Registration No. 10-1384578 (patent document 1) relates to an antimicrobial peptide having a novel amino acid sequence, more particularly to an antimicrobial peptide isolated from abalone, which has antimicrobial activity against *E. coli* or *Staphylococcus aureus*. However, the patent document 1 does not disclose an antimicrobial peptide analogue derived from abalone which is commercially viable because it is composed of 15 or less amino acids and exhibits stronger antimicrobial activity against various bacteria.

REFERENCES OF THE RELATED ART

Patent Documents

Patent document 1. Korean Patent Registration No. 10-1384578.

SUMMARY

The present disclosure is directed to designing and providing an antimicrobial peptide analogue using hdMolluscidin, a peptide derived from abalone (*Haliotis discus*) and has superior antimicrobial activity, which has a decreased number of amino acids to a commercially viable level and exhibits superior antimicrobial activity.

In an aspect, the present disclosure provides an antimicrobial peptide analogue containing: a hydrophobic group containing 1-3 amino acid residues selected from alanine (A), leucine (L) and tryptophan (W); and a hydrophilic group containing 1 or 2 lysine (K) residue(s), wherein 3 or 4 of the hydrophobic group and 2 or 3 of the hydrophilic group are bound alternatingly.

The peptide analogue may form an α-helix structure.

The peptide analogue may consist of 8-15 amino acid residues.

The peptide analogue may contain at least one amino acid sequence KLLK.

If the hydrophobic group is located between the hydrophilic group and the at least one hydrophilic group bound to the hydrophobic group comprises 2 lysine (K) residues, the number of amino acid residues of the hydrophobic group may be 2.

The peptide analogue may have an amino acid sequence selected from a group consisting of SEQ ID NOS 1-11.

The antimicrobial peptide analogue may have an amidated or methylated C-terminal.

The antimicrobial peptide analogue may have an acetylated or palmitoylated N-terminal.

The peptide analogue may have antimicrobial activity against at least one selected from a group consisting of Gram positive bacteria, Gram negative bacteria and yeast.

The peptide analogue may have antimicrobial activity against at least one selected from a group consisting of *Bacillus subtilis, Staphylococcus epidermidis, Staphylococcus mutans, Propionibacterium acnes, E. coli* D31, *E. coli* ML35p, *Shigella flexneri, Pseudomonas aeruginosa, Vibrio parahaemolyticus* and *Candida albicans*.

In another aspect, the present disclosure provides an antimicrobial pharmaceutical composition containing the antimicrobial peptide analogue as an active ingredient.

In another aspect, the present disclosure provides a pharmaceutical composition for preventing and treating an infectious disease caused by bacteria, which contains the antimicrobial peptide analogue as an active ingredient.

In another aspect, the present disclosure provides an antimicrobial cosmetic composition containing the antimicrobial peptide analogue as an active ingredient.

The cosmetic composition may be in the form of a solution, a powder, an emulsion, a lotion, a spray, an ointment, an aerosol, a cream or a foam.

In another aspect, the present disclosure provides an antimicrobial food additive containing the antimicrobial peptide analogue as an active ingredient.

In another aspect, the present disclosure provides a feed additive containing the antimicrobial peptide analogue as an active ingredient.

In another aspect, the present disclosure provides a hygiene product containing the antimicrobial peptide analogue as an active ingredient.

The antimicrobial peptide analogue according to the present disclosure is designed based on hdMolluscidin which is a peptide derived from the gill of abalone and has been designed to be commercially viable by reducing the number of amino acids. Despite the reduced number of amino acids, the designed peptide analogue exhibits very superior antimicrobial activity as well as high membrane permeability and low hemolytic activity.

BRIEF DESCRIPTION OF DRAWINGS

FIG. 1 shows a sequence alignment result of the amino acid sequences of hdMolluscidin (SEQ ID NO: 15), an antimicrobial peptide derived from abalone, and cgMolluscidin (SEQ ID NO: 16), an antimicrobial peptide derived from Pacific oyster.

FIG. 2 shows the amino acid sequences of hdMolluscidin, an antimicrobial peptide derived from abalone, and a parent peptide portion (fragment 1 and fragment 2) for designing the antimicrobial peptide analogue (SEQ ID NO: 15) according to the present disclosure. FIG. 2 shows that the peptide analogue forms an α-helix structure.

DETAILED DESCRIPTION OF EMBODIMENTS

Figure 3:
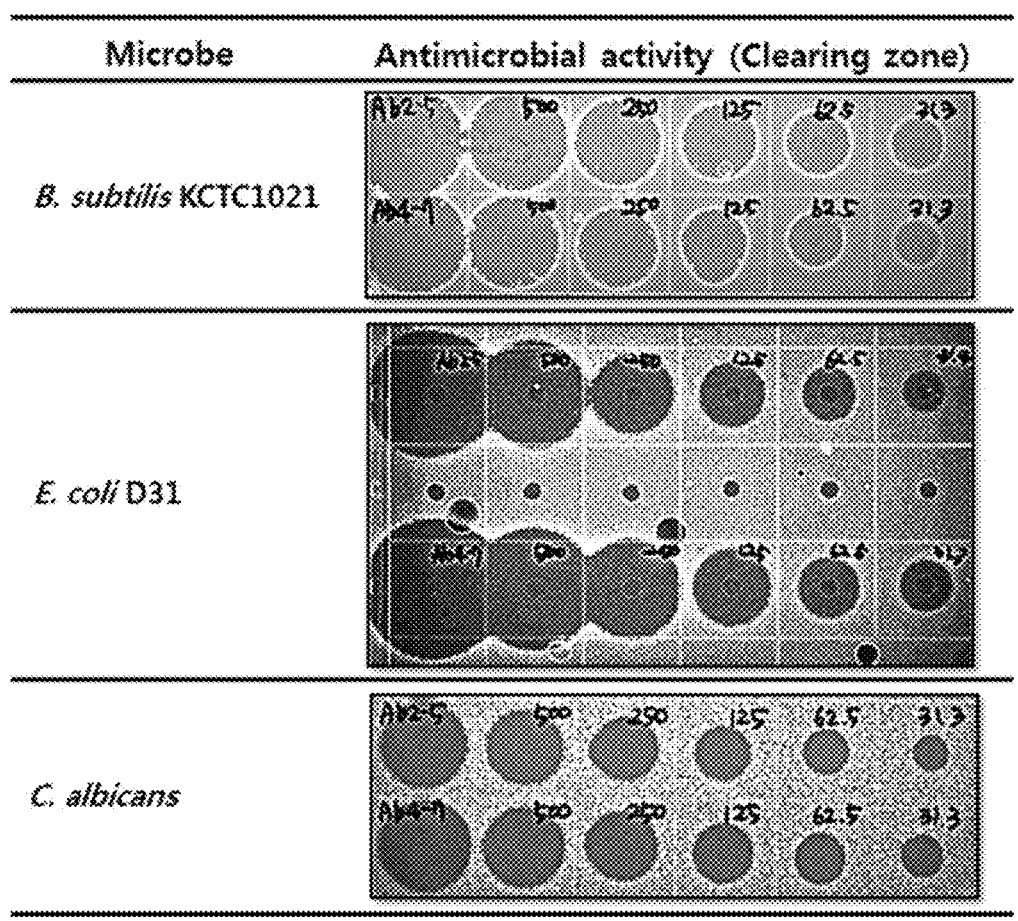
FIG. 3 shows the antimicrobial activity of an antimicrobial peptide analogue according to the present disclosure.

The inventors of the present disclosure have made consistent efforts to develop an antimicrobial peptide analogue derived from abalone (*Haliotis discus*), which has superior antimicrobial activity and is commercially viable, and have completed the present disclosure as a result thereof.

Specifically, the antimicrobial peptide analogue according to the present disclosure contains: a hydrophobic group containing 1-3 amino acid residues selected from alanine (A), leucine (L) and tryptophan (W); and a hydrophilic group containing 1 or 2 lysine (K) residue(s), wherein 3 or 4 of the hydrophobic group and 2 or 3 of the hydrophilic group are bound alternatingly.

The peptide analogue according to the present disclosure is derived from a peptide (hdMolluscidin) which has been extracted and purified from the gill of abalone (*Haliotis discus*). hdMolluscidin is a peptide having a very superior antimicrobial activity. However, hdMolluscidin is not commercially viable because it consists of a total of 46 amino acids. Therefore, the inventors of the present disclosure have developed an antimicrobial peptide analogue derived from hdMolluscidin, which is a peptide derived from abalone, which has superior antimicrobial activity and is commercially viable.

The antimicrobial peptide analogue according to the present disclosure may form an α-helix structure. The peptide analogue forms an α-helix structure when it exhibits amphiphilicity with hydrophilicity and hydrophobicity at the same time. The hydrophilic part improves binding force and the hydrophobic part improves permeability.

First, the inventors of the present disclosure have predicted the secondary structure of hdMolluscidin using a secondary structure prediction program for designing of the peptide analogue. The predicted secondary structure of hdMolluscidin was a combination of a random coil structure, an α-helix structure and a β-sheet structure. Based on the predicted secondary structure, the part of hdMolluscidin with an amphiphilic α-helix structure was selected because it is known as the ideal structure in exhibiting antimicrobial activity. And, the N-terminal part of hdMolluscidin was selected as a parent peptide portion for designing the analogue.

FIG. 2 shows the amino acid sequences of hdMolluscidin, an antimicrobial peptide derived from abalone, and the parent peptide portion (fragment 1 and fragment 2) for designing the antimicrobial peptide analogue according to the present disclosure.

Because each of the fragment 1 (amino acid sequence: AATKPKKAGAEAAP (SEQ ID NO: 12)) and the fragment 2 (amino acid sequence: KPAKKQTKKKP (SEQ ID NO: 13)) does not exhibit amphiphilicity although it forms an α-helix structure, it is necessary to substitute some amino acids so that it can exhibit both hydrophobicity and hydrophilicity at the same time.

If the antimicrobial peptide analogue exhibits amphiphilicity through the amino acid substitution, the hydrophilic part facilitates binding to the cell membrane or DNA and the hydrophobic part facilitates permeation.

When designing the antimicrobial peptide analogue using the fragment 1 or the fragment 2, it is desired that lysine (K), which is a hydrophilic (positively charged) residue, and alanine (A), which is a hydrophobic residue, are retained. Meanwhile, proline (P), threonine (T) and glutamine (Q), which are polar but not electrically charged, may be substituted with another hydrophobic residue, specifically a leucine (L) residue, because they are not desired in terms of antimicrobial activity.

In addition, tryptophan (W), which exhibits high membrane permeability and high resistance to proteases, may be located beside a residue vulnerable to the enzymes such as lysine (K) so as to reduce cutting by the proteases.

The antimicrobial peptide analogue of the present disclosure is designed using the fragment 1 or the fragment 2 as a parent peptide and may contain: a hydrophobic group containing 1-3 amino acid residues selected from alanine (A), leucine (L) and tryptophan (W); and a hydrophilic group containing 1 or 2 lysine (K) residue(s). Specifically, the number of the hydrophobic group may be 3 or 4 and the number of the hydrophilic group may be 2 or 3. Specifically, the hydrophobic group may be bound to 2 or more locations selected from a group consisting of the C-terminal and the N-terminal of the hydrophilic group and between hydrophilic groups. Specifically, the hydrophobic group may consist of 2 or less kinds of amino acid residues.

Specifically, the antimicrobial peptide analogue according to the present disclosure may consist of 8-15 amino acid residues. And, specifically, it may contain at least one amino acid sequence KLLK (SEQ ID NO: 14). If the peptide analogue contains the amino acid sequence 'KLLK' (SEQ ID NO: 14), it is very advantageous in enhancing antimicrobial activity.

Specifically, in the antimicrobial peptide analogue of the present disclosure, if the hydrophobic group is located between the hydrophilic group and the at least one hydrophilic group bound to the hydrophobic group comprises 2 lysine (K) residues, the number of amino acid residues of the hydrophobic group may be 2.

Specifically, an amino group (—NH$_2$) or a methyl group (—CH$_3$) may be added to the C-terminal of the antimicrobial peptide analogue according to the present disclosure. If the C-terminal of the antimicrobial peptide analogue is amidated, resistance to proteases and positive net charge may be further enhanced. And, if it is methylated, in-vivo stability may be increased because resistance to exopeptidases, which cleave the peptide from the terminal, can be increased.

Specifically, the peptide analogue may have an acetylated or palmitoylated N-terminal. If the N-terminal of the antimicrobial peptide analogue is acetylated, much superior antimicrobial activity can be achieved as compared to when it is not and the peptide can be protected from proteolytic degradation. And, if it is palmitoylated, permeability into cells can be enhanced.

The antimicrobial peptide analogue according to the present disclosure exhibits antimicrobial activity and is commercially viable because it has a short amino acid sequence. In addition, the antimicrobial peptide analogue according to the present disclosure has strong inner membrane permeability. That is to say, it is likely that the antimicrobial peptide analogue according to the present disclosure exhibits antimicrobial activity by directly permeating into the inner membrane of bacteria. And, the antimicrobial peptide analogue according to the present disclosure lacks a cytotoxicity problem because it exhibits no hemolytic activity.

The antimicrobial peptide analogue designed and prepared as described above may have antimicrobial activity against one or more selected from a group consisting of bacteria such as Gram positive bacteria, Gram negative bacteria, etc. and fungi such as yeast, molds, etc.

More specifically, the antimicrobial peptide analogue may have antimicrobial activity against one or more selected from a group consisting of four species of Gram positive bacteria (*Bacillus subtilis, Staphylococcus epidermidis, Staphylococcus mutans* and *Propionibacterium acnes*), five species of Gram negative bacteria (*E. coli* D31, *E. coli* ML35p, *Shigella flexneri, Pseudomonas aeruginosa* and *Vibrio parahaemolyticus*) and one yeast species (*Candida albicans*).

The present disclosure also provides an antimicrobial pharmaceutical composition containing the antimicrobial peptide analogue according to the present disclosure as an active ingredient.

A method for administering the pharmaceutical composition is not particularly limited. Specifically, it may be administered intraarterially, intravenously, subcutaneously, intrarectally, intranasally or via any other parenteral route. More specifically, it may be administered intraarterially, intravenously, orally or directly into muscle cells.

The administration dosage of the composition will rely on the activity of the active ingredient, administration route, severity of the condition to be treated, condition and previous disease history of the patient. However, to start with a lower dosage than is required to achieve the desired therapeutic effect and gradually increase the administration dosage until the desired effect is achieved is within the knowledge of the related art and the specific administration dosage may be determined considering the age, sex, body type and body weight. The composition may be further processed before being formulated into a pharmaceutically acceptable pharmaceutical agent. Specifically, it may be pulverized or ground into smaller particles. For a desired effect, an effective dosage of the antimicrobial peptide of the present disclosure may be 1-2 mg/kg, specifically 0.5-1 mg/kg, and the administration may be made 1-3 times a day. However, the scope of the present disclosure is not limited by the administration dosage by any means.

The pharmaceutical composition of the present disclosure may be prepared into a formulation of a unit dosage form or a multiple dosage form using a pharmaceutically acceptable carrier and/or excipient according to a method that can be easily employed by one of ordinary skill in the art to which the present disclosure belongs. The formulation may be an oral formulation such as a powder, a granule, a tablet, a capsule, a suspension, an emulsion, a syrup, an aerosol, etc., a formulation for external application such as an ointment, a cream, etc. or any other pharmaceutical formulation such as a suppository, a sterile solution for injection, etc. and may further contain a dispersant or a stabilizer.

Because the antimicrobial peptide analogue exhibits antimicrobial activity against *Bacillus subtilis, Staphylococcus epidermidis, Staphylococcus mutans, Propionibacterium acnes, E. coli* D31, *E. coli* ML35p, *Shigella flexneri, Pseudomonas aeruginosa, Vibrio parahaemolyticus* and *Candida albicans*, it can prevent or treat the diseases caused by them, such as food poisoning, candidiasis, typhoid, cholera, etc. Therefore, the antimicrobial peptide analogue may be used as an active ingredient in a pharmaceutical composition for preventing or treating the infectious diseases caused by the microorganisms.

The antimicrobial peptide analogue may also be used as an active ingredient of an antimicrobial cosmetic composition. The cosmetic composition may be in the form of a solution, a powder, an emulsion, a lotion, a spray, an ointment, an aerosol, a cream or a foam. The cosmetic composition of the present disclosure may contain a carrier which is acceptable in a cosmetic formulation. The "carrier which is acceptable in a cosmetic formulation" refers to a compound or composition already used in cosmetic formulations or a compound or composition to be developed which lacks toxicity, instability or irritability as to be applicable to human skin.

The carrier may be contained in an amount of about 1-99.99 wt %, specifically about 90-99.99 wt %, based on the total weight of the cosmetic composition of the present disclosure. Examples of the carrier may include an alcohol, an oil, a surfactant, a fatty acid, a silicone oil, a humectant, a moisturizer, a viscosity modifier, an emulsifier, a stabilizer, a sunscreen, a UV absorbent, a colorant, a fragrance, etc. A compound or composition that can be used as the alcohol, oil, surfactant, fatty acid, silicone oil, humectant, moisturizer, viscosity modifier, emulsifier, stabilizer, sunscreen, UV absorbent, colorant or fragrance is known in the art and can be adequately selected by those skilled in the art.

In an exemplary embodiment of the present disclosure, the cosmetic composition according to the present disclosure may contain, in addition to the peptide analogue, glycerin, butylene glycol, propylene glycol, polyoxyethylene hydrogenated castor oil, ethanol, triethanolamine, etc. and may contain a trace amount of an antiseptic, a fragrance, a colorant, purified water, etc., if necessary.

In the present disclosure, the term skin includes not only the face but also the scalp and the whole body. For application to the scalp, the cosmetic composition may be prepared as a shampoo, a rinse, a treatment, a hair restorer, etc. And, for application to the whole body, it may be prepared as a body cleanser, etc.

The antimicrobial peptide analogue may also be used as an active ingredient of an antimicrobial food additive or a feed additive.

In a specific exemplary embodiment of the present disclosure, the antimicrobial peptide according to the present disclosure can be usefully used in an antimicrobial food additive or a feed additive because it has superior antimicrobial activity against not only Gram negative and Gram positive bacteria but also fungi and lacks cytotoxicity.

The food is not particularly limited in its kind. Examples of the food to which the substance can be added include a drink, a meat, a sausage, a bread, a biscuit, a rice cake, a chocolate, a candy, a snack, a pizza, an instant noodle, a noodle, a gum, a diary product including ice cream, a soup, a beverage, an alcoholic beverage, a vitamin supplement and any health functional food. The antimicrobial peptide analogue of the present disclosure may be added to a food as it is or as being mixed with other food or food ingredients. The mixing amount of the active ingredient may be determined adequately depending on the purpose of use (for prevention or improvement). In general, the antimicrobial peptide analogue may be added in an amount of 0.1-20 wt % based on the total weight of the food. However, when the composition is used for health or hygiene or it is used for a long time for the purpose of health control, the amount of the active ingredient may be smaller than the above-described range. Also, the amount of the active ingredient may be larger than the above-described range because it has no safety problem.

In addition, the antimicrobial peptide analogue may be usefully used as an active ingredient of a hygiene product such as a wet wipe, a hand sanitizer, a mouthwash, an oral antiseptic or a toothpaste additive.

Hereinafter, the present disclosure will be described in more detail through specific examples so that one or ordinary skill in the art to which the present disclosure belongs can easily carry out the present disclosure. However, the present disclosure can be embodied in various forms and is not limited by the examples.

Example

<Materials and Methods>
Reagents and Materials

Tryptic soy broth (TSB) and agarose type I (low EEO agar) for measurement of antimicrobial activity were purchased from Merck (Darmstadt, Germany) and Sigma (St. Louis, Mo., USA), respectively. Water and acetonitrile ($CH_3CN$) for HPLC used in purification were purchased from Tedia (Ohio, USA). All other reagents were of analytical grade.

Designing of Antimicrobial Peptide Analogue

In order to design analogues of hdMolluscidin, its secondary structure was predicted using EMBOSS GUI's Garnier and ExPASy Tools' GOR as secondary structure prediction programs. Based on the predicted secondary structure of hdMolluscidin, two fragments exhibiting α-helix structures were selected at the N-terminal side to design the analogues.

The designed analogues consisted of 8-15 amino acids. They were designed through amidation or methylation at the C-terminal, acetylation or palmitoylation at the N-terminal or addition, substitution, removal, etc. of amino acids at specific locations.

Synthesis and Purification of Antimicrobial Peptide Analogue

The designed peptide analogues were synthesized and purified by Peptron Inc. (Daejeon, Korea) to a purity of 95% or higher. The analogues were synthesized by F-moc solid-phase synthesis using the peptide synthesizer ASP48S (Peptron, Daejeon, Korea) and purified by RP-HPLC using the Shiseido Capcell-Pak C18 column (250 mm×4.6 mm, 10 μm). The purification was conducted at 220 nm with a flow rate of 1 mL/min using a $H_2O$—$CH_3CN$ solvent system containing 0.1% (v/v) trifluoroacetic acid with a concentration gradient of 3-40%. The molecular weight of the purified peptide analogues was measured by liquid chromatography/mass spectrometry (LC/MS; HP1100 series; Agilent, Santa Clara, Calif., USA). The purified peptide analogues were dissolved in 0.01% acetic acid to a concentration of 1000 μg/mL and used in the following experiments.

Method for Measuring Antimicrobial Activity and Used Microorganisms

Four species of Gram positive bacteria (*Bacillus subtilis, Staphylococcus epidermidis, Staphylococcus mutans* and *Propionibacterium acnes*), five species of Gram negative bacteria (*E. coli* D31, *E. coli* ML35p, *Shigella flexneri, Pseudomonas aeruginosa* and *Vibrio parahaemolyticus*) and one yeast species (*Candida albicans*) were used for experiments. The antimicrobial activity was measured by ultrasensitive radial diffusion assay (URDA) using two layers of media of different concentrations. First, the microorganisms were pre-cultured in each medium for 18 hours and the concentration of the microorganisms was adjusted to 84% T ($\approx 1 \times 10^8$ CFU/mL) using a colorimeter (Product No. 52-1210, BioMerieux, Inc., USA). Then, 0.5 mL of the diluted microorganism solution was added to an underlay gel containing 9.5 mL of 0.03% TSB, 1% type I agarose and 10 mM phosphate buffer (PB; pH 6.5) and plated and solidified on a plate after mixing well. After boring a well with a diameter of 2.5 mm on the solidified plate using a punch, 5 μL of each analogue solution was introduced. All the analogues were dissolved in 5 μL of 0.01% acetic acid to avoid any effect of solvent. After the analogue permeated into the medium, the microorganisms were cultured for 3 hours and an overlay gel containing 10 mL of 6% TSB, 1% type I agarose and 10 mM phosphate buffer (pH 6.5) was poured and solidified. Then, the microorganisms were cultured again for 18 hours at the same temperature. Next day, the antimicrobial activity was determined by measuring the size (diameter) of a clear zone formed around the well. Piscidin 1, an antimicrobial peptide derived from the mast cells of a hybrid striped bass, was used as a control.

Measurement of Hemolytic Activity

Hemolytic activity was measured using human red blood cells. After adding to human blood an equal amount of phosphate buffered saline (PBS, 50 mM sodium phosphate, 150 mM NaCl, pH 7.4), mixing and centrifuging at 8000×g and 4° C. for 1 minute, the supernatant was removed and the remaining red blood cells were washed 3 times. The red blood cells were added to PBS to a concentration of 3% hematocrit. In order to measure the hemolytic activity, 90 μL of the 3% hematocrit was introduced to an e-tube and then 10 μL of each analogue solution (×10) was added. After incubation of each e-tube at 37° C. for 1 hour, centrifugation was performed at 13,000×g and 4° C. for 10 minutes. After taking 70 μL from each supernatant and transferring to a 96-well microtiter plate, release of hemoglobin was measured at 405 nm. Triton X-100 (0.1%) was used as a control group for 100% lysis of red blood cells and the hemolytic activity was calculated according to the following equation.

% Hemolysis=[(Abs 405 nm in the peptide solution–Abs 405 nm in buffer)/(Abs 405 nm in 0.1% Triton X-100–Abs 405 nm in buffer)]×100

Measurement of Inner Membrane Permeability

The inner membrane permeability was measured by measuring the activity of β-galactosidase present in the cytoplasm of E. coli ML35p using O-nitrophenyl-β-D-galactopyranoside (ONPG) as a non-membrane-permeative chromogenic substrate. Cultured E. coli ML35p in the mid-logarithmic phase was washed with 10 mM sodium phosphate buffer (NaPB, pH 7.4) and then dissolved in the same buffer containing 1.5 mM ONPG. Then, after adding the peptide analogue, the degree of hydrolysis of β-galactosidase released from the E. coli ML35p by the ONPG to O-nitrophenol was measured at 420 nm. Piscidin 1 and 0.01% acetic acid were used as control groups.

Chromogenic Bacteriolytic Plate Assay

In order to investigate the lytic activity of the analogues for bacterial membrane, chromogenic bacteriolytic plate assay was conducted using E. coli ML35p containing a chromosomal IPTG-inducible β-galactosidase gene (Mardones, G., Venegas, A. Chromogenic plate assay distinguishing bacteriolytic from bacteriostatic activity of an antibiotic agent. J Microbiol Methods. 2000, 40(3), 199-206). After inoculating 2 mL of E. coli ML35p to TSB and culturing at 37° C. for 16-18 hours, a mixture of 50 μL of the cultured microorganism solution, 10 μL of 1 mM IPTG and 50 μL of 50 mg/mL X-gal was poured onto TSB containing 0.8% agarose at 42° C. the next day. After boring a well on the solidified plate, 5 μL of each peptide analogue solution was introduced and incubation was conducted for 3 hours. Then, after pouring 2×TSB containing 10 mL of 1.5% agarose to the plate and solidifying, incubation was conducted again for 16-18 hours. After the incubation, the size (diameter) of a clearing zone and the presence or absence of a blue line at the edge portion were investigated.

Measurement of Minimum Inhibitory Concentration (MIC)

The minimum inhibitory concentration of the analogues was measured according to Patrzykat et al.'s method (Patrzykat, A., Gallant, J. W., Seo, J. K., Pytyck, J., Douglas, S. E. Novel antimicrobial peptides derived from flatfish genes. Antimicrob Agents Chemother. 2003, 47(8), 2464-2470). The peptide analogue solutions were prepared by continuous dilution using 100 μg/mL to 3.13 μg/mL of 0.01% HAc and the measurement was made using 96-well polypropylene microtiter plates (Costar; Corning Incorporated, Corning, N.Y., USA). E. coli ML35p used for the measurement was cultured in TSB medium for 16 hours up to the mid-logarithmic phase and then finally diluted to a concentration of $10^6$ CFU/mL using TSB medium. In order to measure the minimum inhibitory concentration, 90 μL of the finally diluted microorganism solution was added to each well of a 96-well plate and then 10 μL of each analogue solution at a concentration of ×10 of the target concentration was added to each well. No analogue was added for a negative control group and piscidin 1 was added for a positive control group. The minimum inhibitory concentration was defined as the concentration of the analogue when no growth of microorganisms was visually observed at all. In order to investigate the mechanism of the antimicrobial activity of the analogues, each analogue corresponding to the minimum inhibitory concentration was taken from the microorganism solution of each well and plated on a TSA plate. After culturing, it was investigated whether the mechanism is bacteriostatic or bactericidal by based on colony formation.

Killing Kinetics Study

For killing kinetics study of the analogues whose bactericidal process was identified, killing rate for each analogue was investigated at 1×MIC and 5×MIC for 60 minutes. For this, the analogue was added to an e-tube containing $10^6$ CFU/mL of E. coli ML35p. While incubating at 37° C., 10 μL of the solution was taken from the tube at predetermined times (5, 10, 20, 30, 40, 50 and 60 minutes after the addition of the analogue) and plated on a TSA plate. Then, the number of formed colonies was counted. As control groups, no analogue or piscidin 1 was added. The killing % for the analogues was represented as the number of formed colonies relative to that when no analogue was added.

EXPERIMENTAL EXAMPLES

Experimental Example 1: Designed hdMolluscidin Analogues 1) hdMolluscidin hdMolluscidin, isolated from the gill of abalone (Haliotis discus), is an antimicrobial peptide consisting of 46 amino acids and having a molecular weight of 4767.2 Da. hdMolluscidin shows high sequence similarity to cgMolluscidin, an antimicrobial peptide derived from the gill of Pacific oyster (FIG. 1). FIG. 1 shows a sequence alignment result of the amino acid sequences of hdMolluscidin and cgMolluscidin. In FIG. 1, the conserved sequences are shown black.

In order to design analogues with shorter length and increased antimicrobial activity, the secondary structure of hdMolluscidin was predicted using a structure prediction program (FIG. 2).

2) Prediction of Secondary Structure of hdMolluscidin

The secondary structure of hdMolluscidin was predicted using ExPASy Tools' GOR method. As a result, it was predicted that hdMolluscidin has a combination of α-helix and random structures (FIG. 2). Based on this result, two portions (fragment 1 and fragment 2) toward the N-terminal exhibiting α-helix structure were selected as parent regions for designing analogues.

3) Primary Structure of hdMolluscidin Analogues

The peptide analogues designed based on the α-helix structure of hdMolluscidin toward the N-terminal are shown in Table 1. Each analogue consisted of 8-15 amino acid residues. The synthesized analogues were identified by measuring molecular weight.

TABLE 1

| SEQ ID NO | Peptide | Sequence |
| --- | --- | --- |
| SEQ ID NO 1 | Ab2-2 | AAWKLLKALAKA |
| SEQ ID NO 2 | Ab2-3 | LLWKLLKLLLK |
| SEQ ID NO 3 | Ab2-4 | LLWKLLKKLLK |
| SEQ ID NO 4 | Ab2-5 | LLWKLLKKL |
| SEQ ID NO 5 | Ab4-1 | KLALKLLKLL |
| SEQ ID NO 6 | Ab4-2 | KAAAKAAKAA |
| SEQ ID NO 7 | Ab4-3 | KLLLKLLKLL |
| SEQ ID NO 8 | Ab4-4 | KLLLKLLKKLL |
| SEQ ID NO 9 | Ab4-5 | KLLKKLLKLL |

TABLE 1-continued

| SEQ ID NO | Peptide | Sequence |
| --- | --- | --- |
| SEQ ID NO 10 | Ab4-7 | KWLLKLLKKL |
| SEQ ID NO 11 | Ab4-8 | LKWLLKLLKLK |

Experimental Example 2: Antimicrobial Activity of hdMolluscidin Analogues

The antimicrobial activity of the analogues and piscidin 1 (antimicrobial peptide derived from a hybrid striped bass) as a control antimicrobial peptide against bacteria and one yeast species was measured by the URDA method. As a result, the analogues of the present disclosure showed strong antimicrobial activity against the microorganisms. Among them, the antimicrobial peptide analogues having amino acid sequences of SEQ ID NO 4 (Ab2-5) and SEQ ID NO 10 (Ab4-7) showed the best antimicrobial activity (FIG. 3).

In order to investigate the antimicrobial spectrum of the analogues, antimicrobial activity was measured for various microorganisms (Tables 2-4). As a result, the peptide analogues of the present disclosure showed antimicrobial activity comparable to that of piscidin 1. In particular, they showed stronger antimicrobial activity against *C. albicans* than piscidin 1.

In addition, whereas the parent peptide hdMolluscidin showed little antimicrobial activity against *C. albicans*, the antimicrobial peptide analogues of the present disclosure showed strong antimicrobial activity against *C. albicans*.

TABLE 2

| | | Minimal effective concentration (μg/mL) | | | | |
| --- | --- | --- | --- | --- | --- | --- |
| Microbe | Gram | SEQ ID NO 1 | SEQ ID NO 2 | SEQ ID NO 3 | SEQ ID NO 4 | Piscidin 1 |
| *B. subtilis* KCTC1021 | + | 20.0 | 16.0 | 14.0 | 5.8 | 7.5 |
| *S. epidermidis* KCTC1917 | + | 17.3 | 18.4 | 17.2 | 5.6 | NT |
| *S. mutans* KCCM40105 | + | 20.3 | 16.3 | 15.8 | 5.5 | 3.2 |
| *Propionibacterium acnes* KCTC11946 | + | 25.0 | 18.0 | 14.5 | 9.4 | NT |
| *E. coli* D31 | − | 22.0 | 16.2 | 19.4 | 13.5 | 3.8 |
| *E. coli* ML35p | − | 23.0 | 12.1 | 13.8 | 8.4 | 2.3 |
| *Shigella flexneri* KCTC2009 | − | 28.0 | 11.6 | 10.0 | 8.7 | 8.0 |
| *P. aeruginosa* KCTC2004 | − | 36.0 | 14.2 | 15.2 | 10.7 | 8.0 |
| *Vibrio parahaemolyticus* KCCM42264 | | 26.3 | 14.0 | 9.1 | 5.3 | 3.0 |
| *C. albicans* KCCM42264 | Yeast | 42.0 | 17.0 | 15.0 | 10.0 | >62.5 |

TABLE 3

| | | Minimal effective concentration (μg/mL) | | | | |
| --- | --- | --- | --- | --- | --- | --- |
| Microbe | Gram | SEQ ID NO 5 | SEQ ID NO 6 | SEQ ID NO 7 | SEQ ID NO 8 | Piscidin 1 |
| *B. subtilis* KCTC1021 | + | 15.2 | >50.0 | 11.2 | 10.3 | 7.5 |
| *S. epidermidis* KCTC1917 | + | 16.4 | >50.0 | 8.8 | 9.6 | NT |
| *S. mutans* KCCM40105 | + | 10.5 | >50.0 | 7.8 | 7.4 | 3.2 |
| *Propionibacterium acnes* KCTC11946 | + | 16.6 | >50.0 | 11.9 | 12.3 | NT |
| *E. coli* D31 | − | 17.5 | >50.0 | 13.2 | 14.2 | 3.8 |
| *E. coli* ML35p | − | 10.5 | >50.0 | 8.8 | 9.8 | 2.3 |
| *Shigella flexneri* KCTC2009 | − | 17.9 | >50.0 | 10.4 | 10.7 | 8.0 |
| *P. aeruginosa* KCTC2004 | − | 19.9 | >50.0 | 11.2 | 12.5 | 8.0 |
| *Vibrio parahaemolyticus* KCCM42264 | | 8.1 | >50.0 | 6.8 | 7.1 | 3.0 |
| *C. albicans* KCTC7965 | Yeast | 14.4 | >50.0 | 12.1 | 11.8 | >62.5 |

TABLE 4

| Microbe | Gram | Minimal effective concentration (μg/mL) | | | |
|---|---|---|---|---|---|
| | | SEQ ID NO 9 | SEQ ID NO 10 | SEQ ID NO 11 | Piscidin 1 |
| B. subtilis KCTC1021 | + | 15.7 | 9.6 | 12.1 | 7.5 |
| S. epidermidis KCTC1917 | + | 14.0 | 4.6 | 16.0 | NT |
| S. mutans KCCM40105 | + | 9.0 | 4.1 | 12.0 | 3.2 |
| Propionibacterium acnes KCTC11946 | + | 18.5 | 6.2 | 13.1 | NT |
| E. coli D31 | − | 18.9 | 12.2 | 14.1 | 3.8 |
| E. coli ML35p | − | 17.2 | 9.9 | 15.0 | 2.3 |
| Shigella flexneri KCTC2009 | − | 15.4 | 8.7 | 11.2 | 8.0 |
| P. aeruginosa KCTC2004 | − | 17.8 | 7.2 | 8.7 | 8.0 |
| Vibrio parahaemolyticus KCCM42264 | | 9.5 | 4.7 | 9.0 | 3.0 |
| C. albicans KCTC7965 | Yeast | 14.0 | 7.4 | 10.0 | >62.5 |

Experimental Example 3: Hemolytic Activity of hdMolluscidin Analogues

Figure 4A:
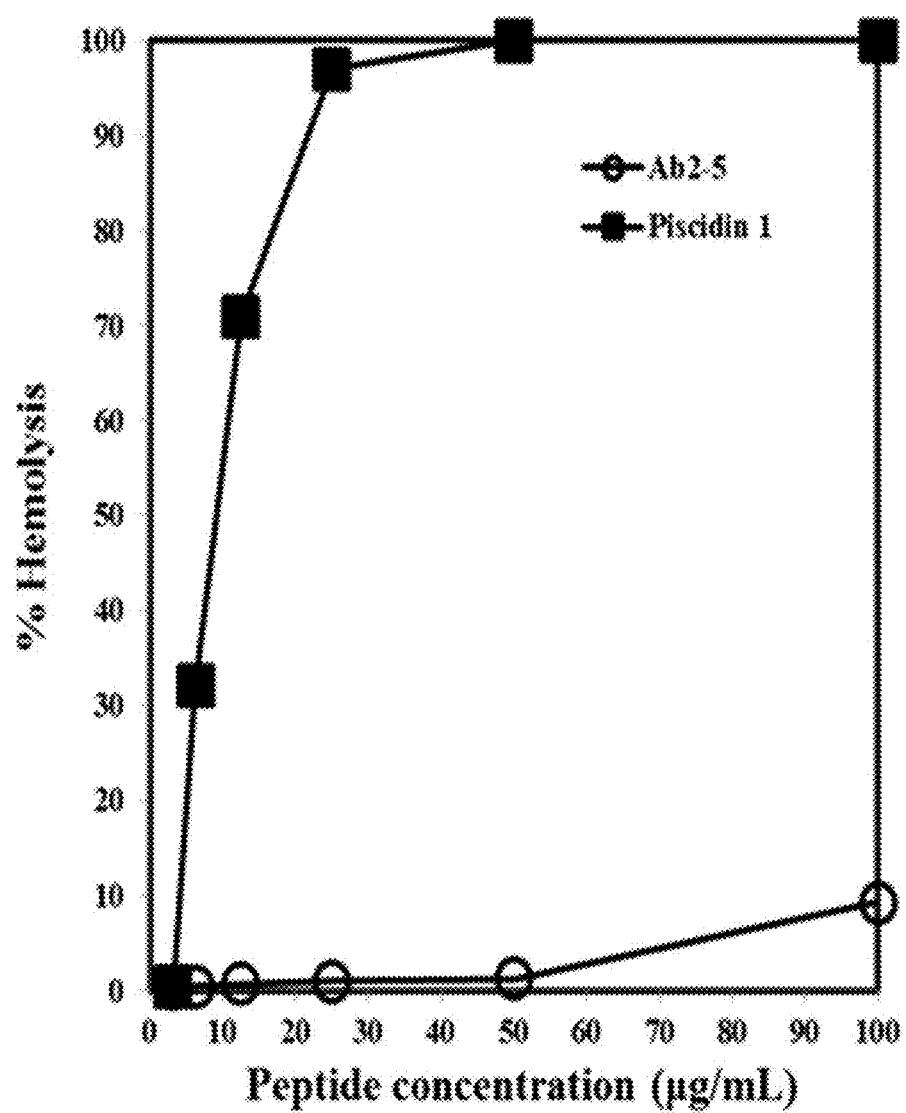
FIG. 4A shows a result of measuring the hemolytic activity of an antimicrobial peptide analogue, Ab2-5 according to the present disclosure and piscidin 1 against human red blood cells.
Figure 4B:
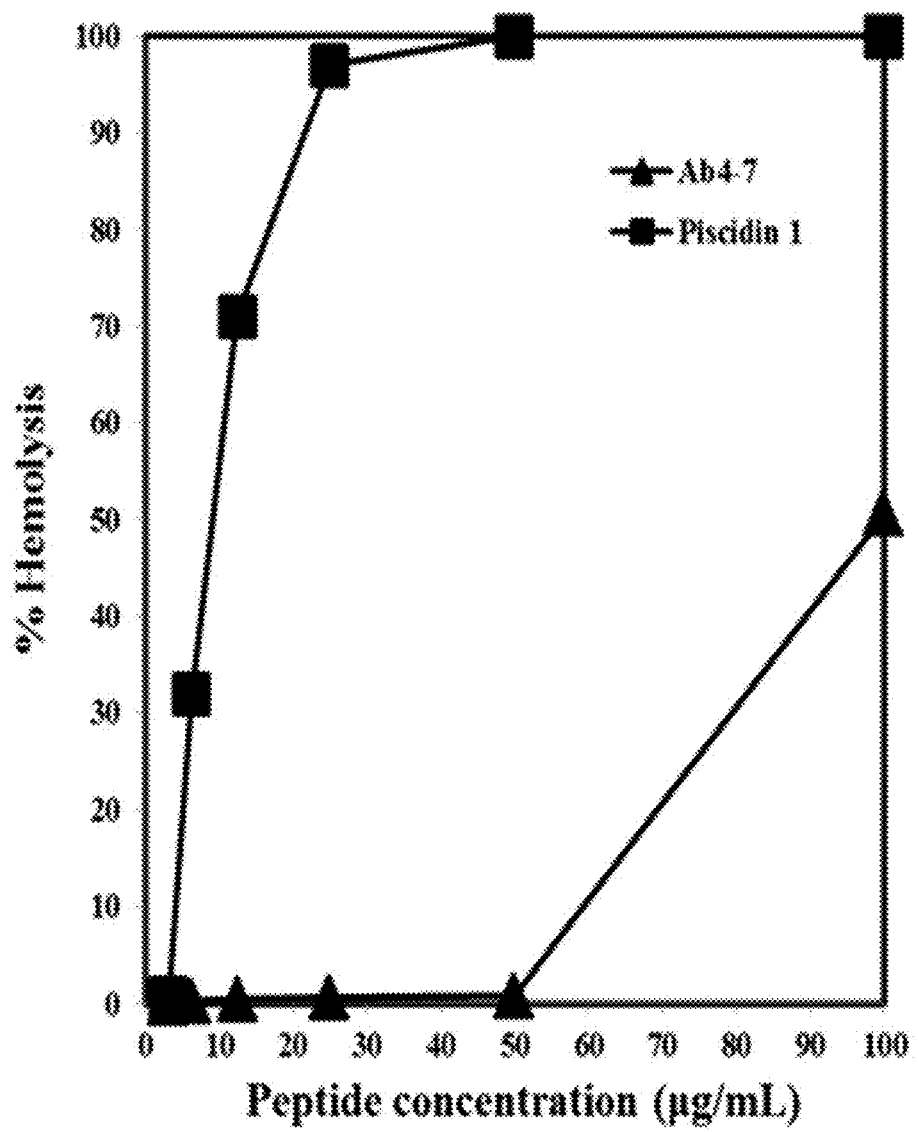
FIG. 4B shows a result of measuring the hemolytic activity of an antimicrobial peptide analogue, Ab4-7 according to the present disclosure and piscidin 1 against human red blood cells.

In order to investigate the toxicity of the hdMolluscidin analogues, the hemolytic activity of the analogues and piscidin 1 as a control antimicrobial peptide against human red blood cells (blood type B) was measured. The peptide analogues of SEQ ID NO 4 and SEQ ID NO 10 showed good hemolytic activity (FIG. 4).

The peptide analogues of the present disclosure showed little hemolytic activity up to the concentration of 50 μg/mL. At the concentration of 100 μg/mL, SEQ ID NO 4 (Ab2-5) showed about 10% of hemolytic activity and SEQ ID NO 10 (Ab4-7) showed about 50% of hemolytic activity against human red blood cells. In contrast, piscidin 1 showed strong hemolytic activity at 12.5 μg/mL. This result suggests that, unlike piscidin 1 which has strong hemolytic activity, the analogues of the present disclosure show little toxicity against human red blood cells at effective concentrations (<50 μg/mL).

Experimental Example 4: Cytoplasmic Membrane Permeabilization

Figure 5A:
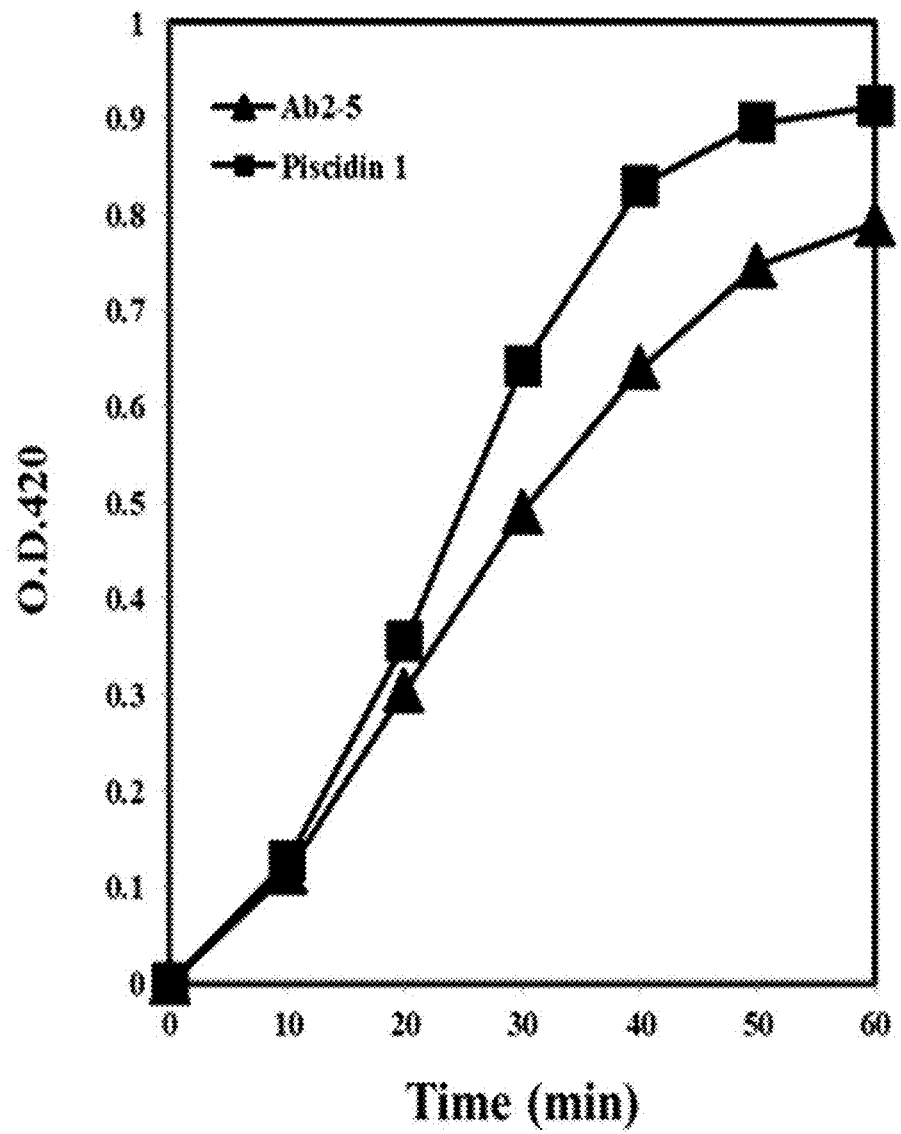
FIG. 5A shows a result of measuring the membrane permeability of an antimicrobial peptide analogue, Ab2-5 according to the present disclosure and piscidin 1 for *E. coli*.
Figure 5B:
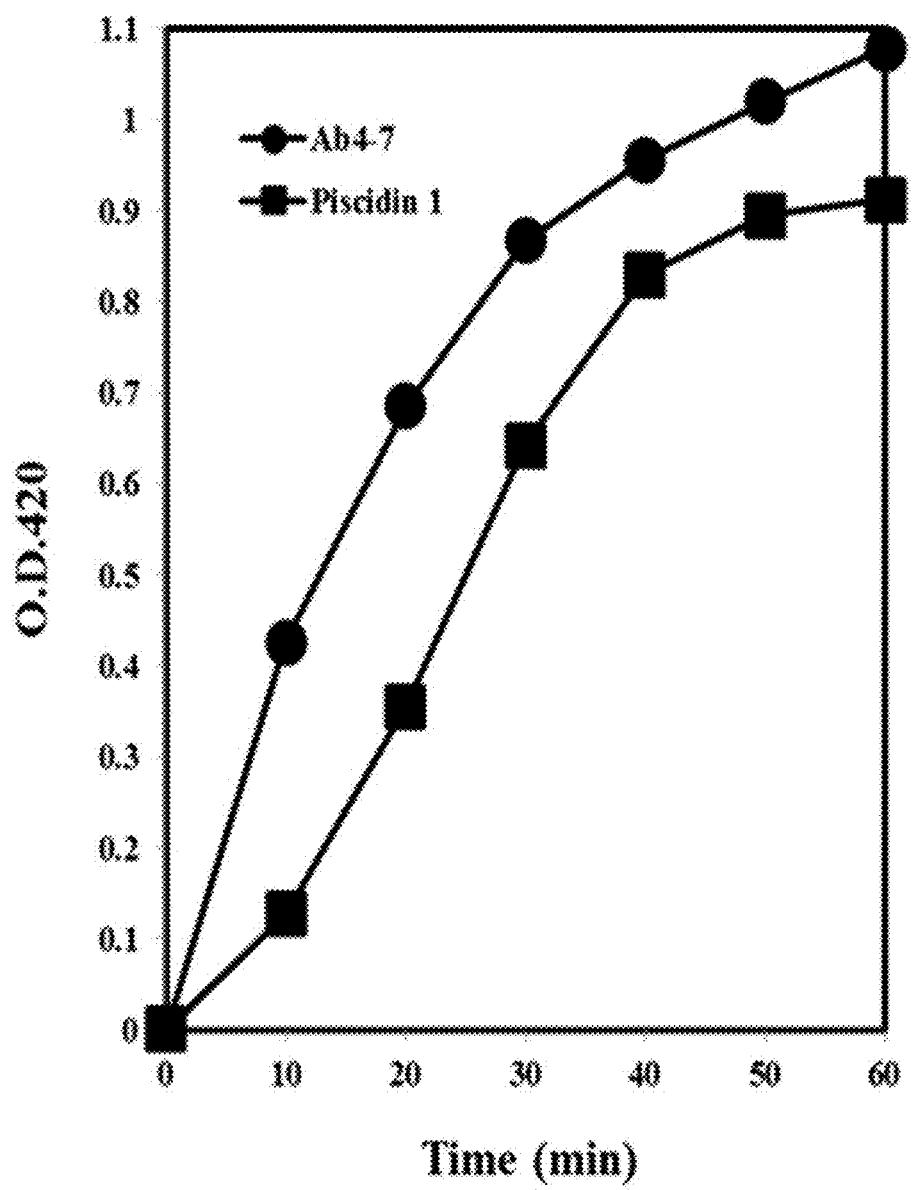
FIG. 5B shows a result of measuring the membrane permeability of an antimicrobial peptide analogue, Ab4-7 according to the present disclosure and piscidin 1 for *E. coli*.

In order to investigate the permeability of the hdMolluscidin analogues and piscidin 1 as a control antimicrobial peptide to the bacterial inner membrane, membrane permeability was measured for E. coli ML35p (FIG. 5). As a result, piscidin 1 showed strong inner membrane permeability for E. coli ML35p in a time-dependent manner. The analogues of the present disclosure also showed strong inner membrane permeability for E. coli ML35p in a time-dependent manner similarly to piscidin 1.

This result suggests that the hdMolluscidin analogues of the present disclosure are likely to exhibit antimicrobial activity by directly permeating into the bacterial inner membrane.

Experimental Example 5: Chromogenic Bacteriolytic Plate Assay

Figure 6:
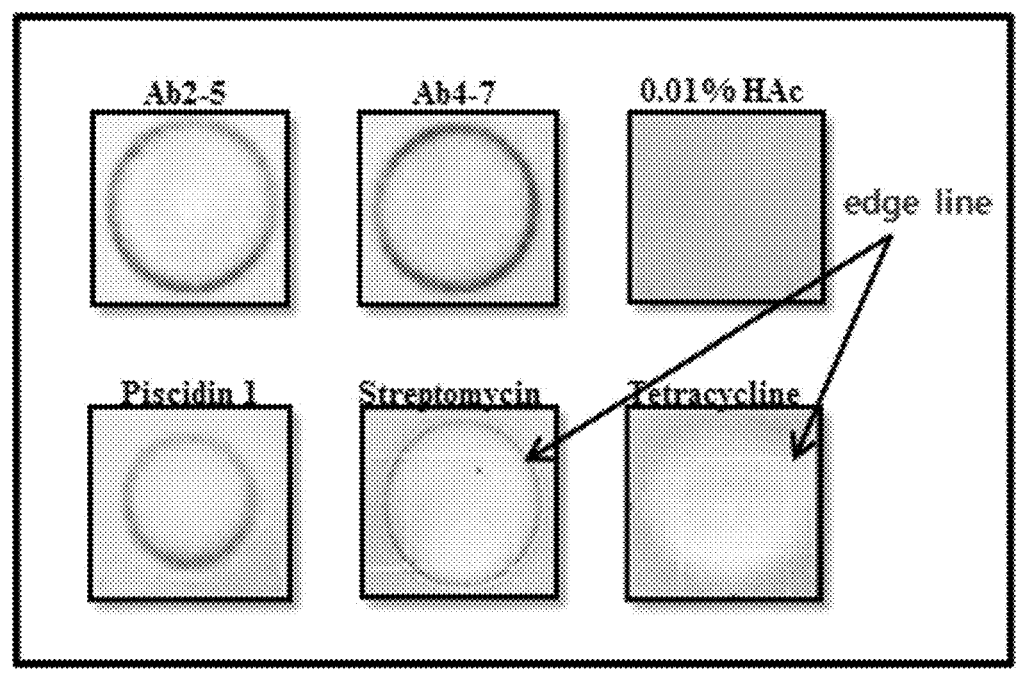
FIG. 6 shows a chromogenic bacteriolytic plate assay result of an antimicrobial peptide analogue according to the present disclosure.

In order to investigate the mechanism of antimicrobial activity of the analogues, chromogenic bacteriolytic plate assay was conducted using E. coli ML35p containing a chromosomal IPTG-inducible β-galactosidase gene (FIG. 6). As a result, whereas the antibiotic streptomycin known to exhibit chromogenic bacteriolytic activity against E. coli ML35p showed a blue line at the edge portion, tetracycline known not to exhibit bacteriolytic activity showed no blue line at the edge portion. Piscidin 1 used as a control substance showed an edge line and the peptide analogues of the present disclosure of SEQ ID NO 4 (Ab2-5) and SEQ ID NO 10 (Ab4-7) also showed bacteriolytic activity because blue lines were observed at the edge portion.

This result suggests that the two analogues of the present disclosure lyse the bacterial membrane.

Experimental Example 6: Measurement of Minimum Inhibitory Concentration (MIC) and Minimum Bactericidal Concentration (MBC)

Minimum inhibitory concentration (MIC) and minimum bactericidal concentration (MBC) were measured in order to investigate whether the antimicrobial activity of the analogues is bacteriostatic or bactericidal. As a result, the peptide analogues of the present disclosure showed low MIC for E. coli ML35p similarly to piscidin 1 (Tables 5-7).

TABLE 5

| Microbes | Gram | Minimum inhibitory concentration (MIC) (μg/mL) | | | | |
|---|---|---|---|---|---|---|
| | | SEQ ID NO 1 | SEQ ID NO 2 | SEQ ID NO 3 | SEQ ID NO 4 | Piscidin 1 |
| E. coli ML35p | − | 50.0 | 25.0 | 25.0 | 12.5 | 12.5 |

TABLE 6

| Microbes | Gram | Minimum inhibitory concentration (MIC) (μg/mL) | | | | |
|---|---|---|---|---|---|---|
| | | SEQ ID NO 5 | SEQ ID NO 6 | SEQ ID NO 7 | SEQ ID NO 8 | SEQ ID NO 9 |
| E. coli ML35p | − | 25 | >50 | 12.5 | 12.5 | 25 |

TABLE 7

| Microbes | Gram | Minimum inhibitory concentration (MIC) (μg/mL) | |
|---|---|---|---|
| | | SEQ ID NO 10 | SEQ ID NO 11 |
| E. coli ML35p | − | 6.25 | 25 |

Figure 7A:
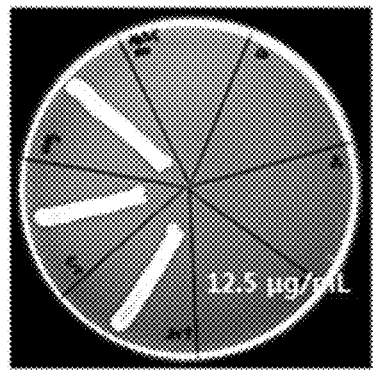
FIG. 7A shows a result of measuring the minimum inhibitory concentration (MIC) and minimum bactericidal concentration (MBC) of an antimicrobial peptide analogue, Ab2-5 according to the present disclosure and piscidin 1 for *E. coli*.
Figure 7B:
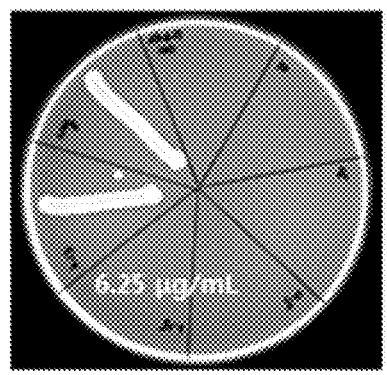
FIG. 7B shows a result of measuring the minimum inhibitory concentration (MIC) and minimum bactericidal concentration (MBC) of an antimicrobial peptide analogue, Ab4-7 according to the present disclosure for *E. coli*.
Figure 7C:
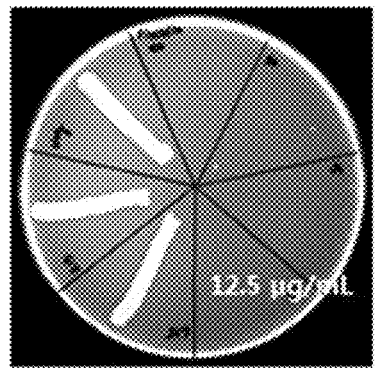
FIG. 7C shows a result of measuring the minimum inhibitory concentration (MIC) and minimum bactericidal concentration (MBC) of piscidin 1 for *E. coli*.

MBC was measured based on the MIC measurement. As a result, the analogues and piscidin 1 showed the same MBC values as the MIC values (FIG. 7, Tables 8-10). This result suggests that the minimum inhibitory concentration (MIC) of the peptide analogues of the present disclosure is identical to the minimum bactericidal concentration (MBC), which means that the antimicrobial activity is achieved through a bactericidal process.

TABLE 8

| Microbes | Gram | Minimum bactericidal concentration (MBC) (μg/mL) | | | | |
|---|---|---|---|---|---|---|
| | | SEQ ID NO 1 | SEQ ID NO 2 | SEQ ID NO 3 | SEQ ID NO 4 | Piscidin 1 |
| E. coli ML35p | − | 50.0 | 25.0 | 25.0 | 12.5 | 12.5 |

TABLE 9

| Microbes | Gram | Minimum bactericidal concentration (MBC) (μg/mL) | | | | |
| --- | --- | --- | --- | --- | --- | --- |
| | | SEQ ID NO 5 | SEQ ID NO 6 | SEQ ID NO 7 | SEQ ID NO 8 | SEQ ID NO 9 |
| E. coli ML35p | – | 25 | >50 | 12.5 | 12.5 | 25 |

TABLE 10

| Microbes | Gram | Minimum bactericidal concentration (MBC) (μg/mL) | |
| --- | --- | --- | --- |
| | | SEQ ID NO 10 | SEQ ID NO 11 |
| E. coli ML35p | – | 6.25 | 25.0 |

Experimental Example 7: Killing Kinetics Study of Analoques

Figure 8A:
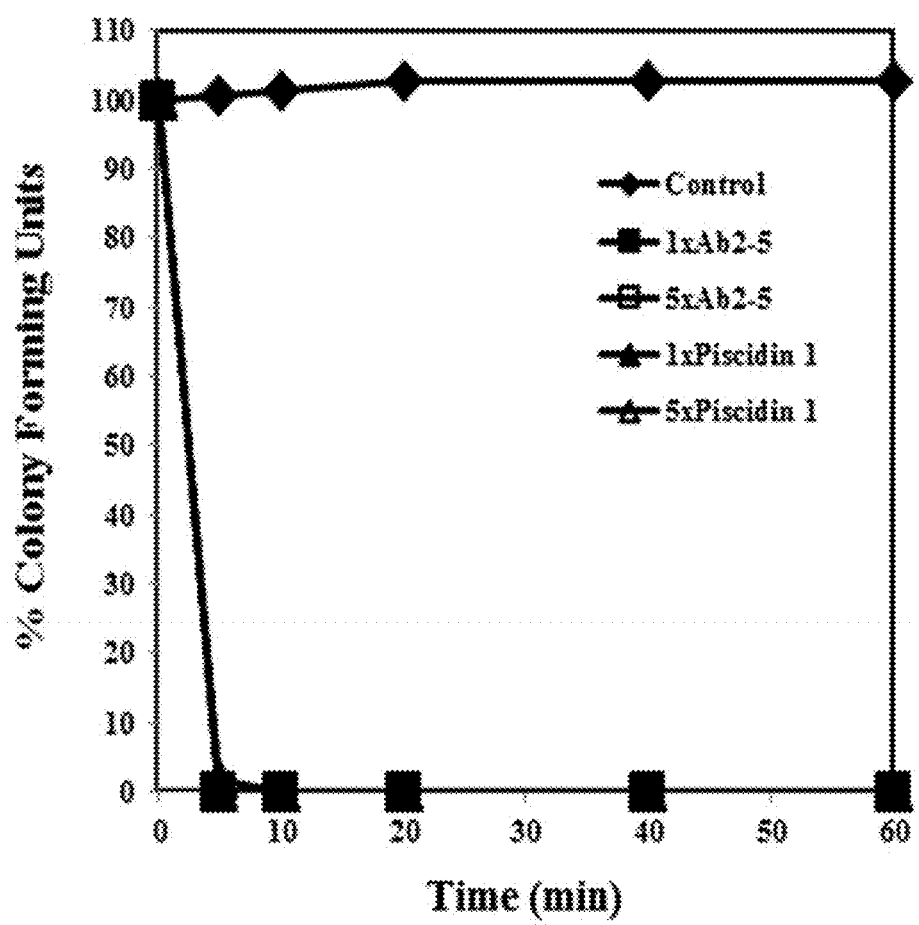
FIG. 8A shows a result of killing kinetics study of an antimicrobial peptide analogue, Ab2-5 according to the present disclosure and piscidin 1 at 1×MIC and 5×MIC for *E. coli*.
Figure 8B:
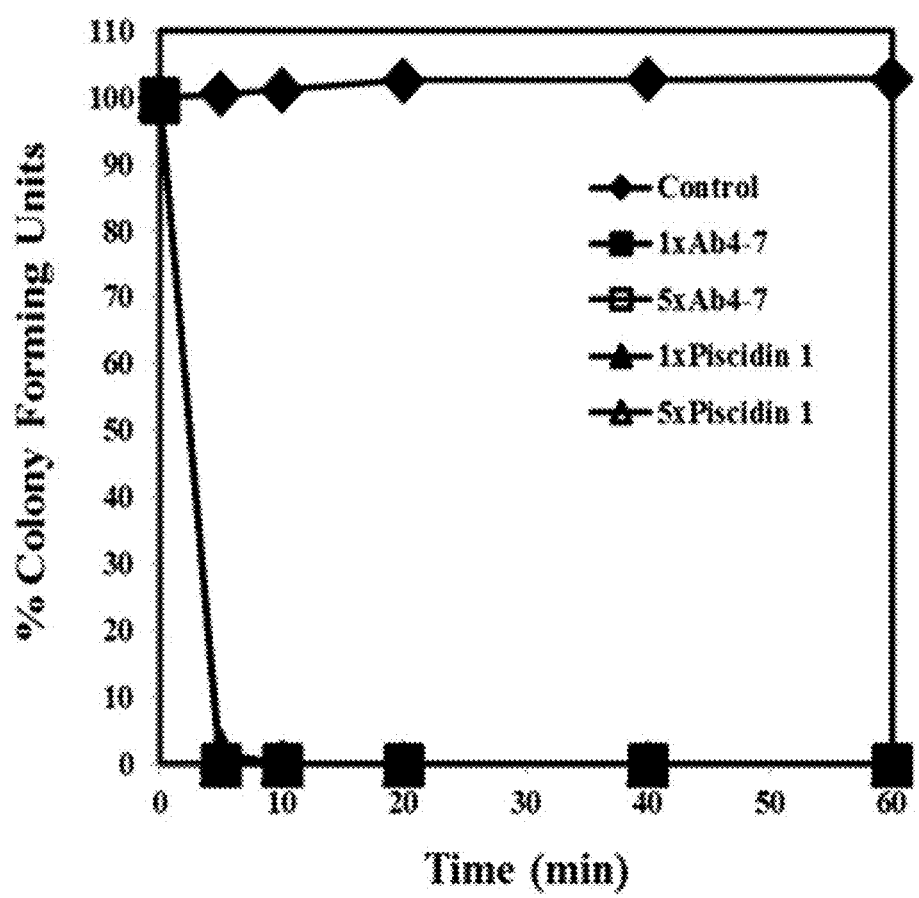
FIG. 8B shows a result of killing kinetics study of an antimicrobial peptide analogue, Ab4-7 according to the present disclosure and piscidin 1 at 1×MIC and 5×MIC for *E. coli*.

In order to investigate the killing kinetics of the analogues with time, the analogues were incubated at 1×MIC and 5×MIC for 60 minutes with E. coli ML35p and then killing kinetics study was conducted (FIG. 8). As a result, all the peptide analogues of the present disclosure killed E. coli ML35p within 5 minutes at the concentrations of 1×MIC and 5×MIC. Piscidin 1, which was used as a control substance, killed E. coli ML35p within 20 minutes at 1×MIC and within 5 minutes at 5×MIC. This result suggests that the peptide analogues of the present disclosure kill the bacteria very quickly (within 5 minutes) after contacting with the bacteria. Therefore, it is though that the analogues directly permeate into the inner membrane of the bacteria and kill them quickly by boring pores on the membrane.

<Result>

In order to obtain new antimicrobial peptide analogues with shorter length and improved activity from a parent antimicrobial peptide with a known primary structure, the inventors of the present disclosure have designed and synthesized peptide analogues by solid-phase synthesis from hdMolluscidin, an antimicrobial peptide isolated from the gill of abalone. The peptide analogues of the present disclosure were prepared by selecting a parent region from the N-terminal of hdMolluscidin, applying substitution, addition or removal of amino acids and amidating or methylating the C-terminal and/or acetylating or palmitoylating the N-terminal. The peptide analogues of the present disclosure showed strong antimicrobial activity and exhibited little hemolytic activity for red blood cells at concentrations exhibiting antimicrobial activity. The analogues were demonstrated to directly bind to the membrane of bacteria and kill the bacteria by permeating into the inner membrane. The peptide analogues of the present disclosure are expected to be utilized as candidate substances for replacing existing antibiotics.

Hereinafter, formulation examples of the peptide analogue of the present disclosure are described.

<Formulation Example 1> Pharmaceutical Agents

<1-1> Powder

| | |
| --- | --- |
| Peptide analogue of the present disclosure | 20 mg |
| Lactose | 20 mg |

A powder was prepared by mixing the above ingredients and filling in a sealed pouch.

<1-2> Tablet

| | |
| --- | --- |
| Peptide analogue of the present disclosure | 10 mg |
| Corn starch | 100 mg |
| Lactose | 100 mg |
| Magnesium stearate | 2 mg |

A tablet was prepared by mixing the above ingredients and tableting according to a commonly employed method.

<1-3> Capsule

| | |
| --- | --- |
| Peptide analogue of the present disclosure | 10 mg |
| Crystalline cellulose | 3 mg |
| Lactose | 14.8 mg |
| Magnesium stearate | 0.2 mg |

A capsule was prepared by mixing the above ingredients and filling in a gelatin capsule according to a commonly employed method.

<1-4> Liquid

| | |
| --- | --- |
| Peptide analogue of the present disclosure | 20 mg |
| Isomerized sugar | 10 g |
| Mannitol | 5 g |
| Purified water | adequate |

According to a commonly employed method, the above ingredients were added to and dissolved in purified water and an adequate amount of lemon flavor was added. After making the final volume 100 mL by adding purified water, the resulting liquid was filled in a brown bottle and sterilized.

<1-5> Injection

| | |
| --- | --- |
| Peptide analogue of the present disclosure | 10 μg/mL |
| Dilute HCl BP | to pH 7.6 |
| Sodium chloride BP | up to 1 mL |

The peptide analogue of the present disclosure was dissolved in an adequate volume of sodium chloride BP. After adjusting the pH of the resulting solution to pH7.6 using dilute HCl BP, the final volume was adjusted using sodium chloride BR After sufficient mixing, the resulting solution was filled in a 5-mL type I ampoule and the ampoule was sealed by melting. Then, an injection was prepared by sterilizing the solution in an autoclave at 120° C. for at least 15 minutes.

<Formulation Example 2> Cosmetics

<2-1> Softening lotion (skin lotion)

An antibacterial softening lotion containing the peptide analogue of the present disclosure was prepared according to a commonly employed method as described in [Table 5].

TABLE 5

| Ingredients | Contents (wt %) |
| --- | --- |
| Peptide analogue of the present disclosure | 0.1-30% |
| 1,3-Butylene glycol | 3.0 |
| Glycerin | 5.0 |
| Polyoxyethylene (60) hydrogenated castor oil | 0.2 |
| Ethanol | 8.0 |

TABLE 5-continued

| Ingredients | Contents (wt %) |
| --- | --- |
| Citric acid | 0.02 |
| Sodium citrate | 0.06 |
| Antiseptic | trace |
| Fragrance | trace |
| Purified water | To 100 |

<2-2> Nourishing lotion (milk lotion)

An antibacterial nourishing lotion containing the peptide analogue of the present disclosure was prepared according to a commonly employed method as described in [Table 6].

TABLE 6

| Ingredients | Contents (wt %) |
| --- | --- |
| Peptide analogue of the present disclosure | 0.1-30% |
| 1,3-Butylene glycol | 3.0 |
| Glycerin | 5.0 |
| Squalane | 10.0 |
| Polyoxyethylene sorbitan monooleate | 2.0 |
| Guaiacum oil | 0.1-30% |
| Polyoxyethylene (60) hydrogenated castor oil | 0.2 |
| Ethanol | 8.0 |
| Citric acid | 0.02 |
| Sodium citrate | 0.06 |
| Antiseptic | trace |
| Fragrance | trace |
| Purified water | To 100 |

<2-3> Cleansing foam

An antibacterial cleansing foam containing the peptide analogue of the present disclosure was prepared according to a commonly employed method as described in [Table 7].

TABLE 7

| Ingredients | Contents (wt %) |
| --- | --- |
| Peptide analogue of the present disclosure | 0.1-30% |
| Sodium N-acylglutamate | 20.0 |

TABLE 7-continued

| Ingredients | Contents (wt %) |
| --- | --- |
| Glycerin | 10.0 |
| PEG 400 | 15.0 |
| Propylene glycol | 10.0 |
| POE (15) oleyl alcohol ether | 3.0 |
| Laurin derivative | 2.0 |
| Methyl paraben | 0.2 |
| EDTA-4Na | 0.03 |
| Fragrance | 0.2 |
| Purified water | To 100 |

<2-4> Nourishing cream

An antibacterial nourishing cream containing the peptide analogue of the present disclosure was prepared according to a commonly employed method as described in [Table 8].

TABLE 8

| Ingredients | Contents (wt %) |
| --- | --- |
| Peptide analogue of the present disclosure | 0.1-30% |
| Vaseline | 7.0 |
| Liquid paraffin | 10.0 |
| Beeswax | 2.0 |
| Polysorbate 60 | 2.5 |
| Sorbitan sesquioleate | 1.5 |
| Squalane | 3.0 |
| Propylene glycol | 6.0 |
| Glycerin | 4.0 |
| Triethanolamine | 0.5 |
| Xanthan gum | 0.5 |
| Tocopheryl acetate | 0.1 |
| Flavor and antiseptic | trace |
| Purified water | To 100 |

While the present disclosure has been described with respect to the specific embodiments, it will be apparent to those skilled in the art that various changes and modifications may be made without departing from the spirit and scope of the disclosure as defined in the following claims.

---

What is claimed is:

1. An antimicrobial peptide analogue consisting of an amino acid sequence selected from the group consisting of SEQ ID NOs: 1-5 and 7-11.

2. The antimicrobial peptide analogue according to claim 1, wherein the antimicrobial peptide analogue forms an α-helix structure.

3. The antimicrobial peptide analogue according to claim 1, wherein the antimicrobial peptide analogue further has an amidated or methylated C-terminus.

4. The antimicrobial peptide analogue according to claim 1, wherein the antimicrobial peptide analogue further has an acetylated or palmitoylated N-terminus.

5. The antimicrobial peptide analogue according to claim 1, wherein the peptide analogue has antimicrobial activity against at least one selected from the group consisting of Gram positive bacteria, Gram negative bacteria and yeast.

6. The antimicrobial peptide analogue according to claim 1, wherein the peptide analogue has antimicrobial activity against at least one selected from the group consisting of *Bacillus subtilis, Staphylococcus epidermidis, Staphylococcus mutans, Propionibacterium acnes, Escherichia coli* (*E. coli*) D31, *E. coli* ML35p, *Shigella flexneri, Pseudomonas aeruginosa, Vibrio parahaemolyticus* and *Candida albicans*.

7. An antimicrobial pharmaceutical composition comprising the antimicrobial peptide analogue of claim 1 as an active ingredient.

8. A pharmaceutical composition for treating an infectious disease caused by bacteria comprising the antimicrobial peptide analogue of claim 1 as an active ingredient.

9. An antimicrobial cosmetic composition comprising the antimicrobial peptide analogue of claim 1 as an active ingredient.

10. The composition according to claim 9, wherein the composition is in the form of a solution, a powder, an emulsion, a lotion, a spray, an ointment, an aerosol, a cream or a foam.

11. An antimicrobial food additive comprising the antimicrobial peptide analogue of claim 1 as an active ingredient.

12. A feed additive comprising the antimicrobial peptide analogue of claim 1 as an active ingredient.

13. A hygiene product comprising the antimicrobial peptide analogue of claim 1 as an active ingredient.

* * * * *

SEQUENCE LISTING

<160> NUMBER OF SEQ ID NOS: 17

<210> SEQ ID NO 1
<211> LENGTH: 12
<212> TYPE: PRT
<213> ORGANISM: Haliotis discus

<400> SEQUENCE: 1

Ala Ala Trp Lys Leu Leu Lys Ala Leu Ala Lys Ala
1               5                   10

<210> SEQ ID NO 2
<211> LENGTH: 11
<212> TYPE: PRT
<213> ORGANISM: Haliotis discus

<400> SEQUENCE: 2

Leu Leu Trp Lys Leu Leu Lys Leu Leu Leu Lys
1               5                   10

<210> SEQ ID NO 3
<211> LENGTH: 11
<212> TYPE: PRT
<213> ORGANISM: Haliotis discus -continued

```
<400> SEQUENCE: 3

Leu Leu Trp Lys Leu Leu Lys Lys Leu Leu Lys
1               5                   10

<210> SEQ ID NO 4
<211> LENGTH: 9
<212> TYPE: PRT
<213> ORGANISM: Haliotis discus

<400> SEQUENCE: 4

Leu Leu Trp Lys Leu Leu Lys Lys Leu
1               5

<210> SEQ ID NO 5
<211> LENGTH: 10
<212> TYPE: PRT
<213> ORGANISM: Haliotis discus

<400> SEQUENCE: 5

Lys Leu Ala Leu Lys Leu Leu Lys Leu Leu
1               5                   10

<210> SEQ ID NO 6
<211> LENGTH: 10
<212> TYPE: PRT
<213> ORGANISM: Haliotis discus

<400> SEQUENCE: 6

Lys Ala Ala Ala Lys Ala Ala Lys Ala Ala
1               5                   10

<210> SEQ ID NO 7
<211> LENGTH: 10
<212> TYPE: PRT
<213> ORGANISM: Haliotis discus

<400> SEQUENCE: 7

Lys Leu Leu Leu Lys Leu Leu Lys Leu Leu
1               5                   10

<210> SEQ ID NO 8
<211> LENGTH: 11
<212> TYPE: PRT
<213> ORGANISM: Haliotis discus

<400> SEQUENCE: 8

Lys Leu Leu Leu Lys Leu Leu Lys Lys Leu Leu
1               5                   10

<210> SEQ ID NO 9
<211> LENGTH: 10
<212> TYPE: PRT
<213> ORGANISM: Haliotis discus

<400> SEQUENCE: 9

Lys Leu Leu Lys Lys Leu Leu Lys Leu Leu
1               5                   10

<210> SEQ ID NO 10
<211> LENGTH: 10
<212> TYPE: PRT
<213> ORGANISM: Haliotis discus

<400> SEQUENCE: 10
```

```
<210> SEQ ID NO 11
<211> LENGTH: 11
<212> TYPE: PRT
<213> ORGANISM: Haliotis discus

<400> SEQUENCE: 11

Lys Trp Leu Leu Lys Leu Leu Lys Lys Leu
1               5                   10

<210> SEQ ID NO 11
<211> LENGTH: 11
<212> TYPE: PRT
<213> ORGANISM: Haliotis discus

<400> SEQUENCE: 11

Leu Lys Trp Leu Leu Lys Leu Leu Lys Leu Lys
1               5                   10

<210> SEQ ID NO 12
<211> LENGTH: 14
<212> TYPE: PRT
<213> ORGANISM: Haliotis discus

<400> SEQUENCE: 12

Ala Ala Thr Lys Pro Lys Lys Ala Gly Ala Glu Ala Ala Pro
1               5                   10

<210> SEQ ID NO 13
<211> LENGTH: 11
<212> TYPE: PRT
<213> ORGANISM: Haliotis discus

<400> SEQUENCE: 13

Lys Pro Ala Lys Lys Gln Thr Lys Lys Lys Pro
1               5                   10

<210> SEQ ID NO 14
<211> LENGTH: 4
<212> TYPE: PRT
<213> ORGANISM: Unknown
<220> FEATURE:
<223> OTHER INFORMATION: Description of Unknown:
      Antimicrobial peptide analogue

<400> SEQUENCE: 14

Lys Leu Leu Lys
1

<210> SEQ ID NO 15
<211> LENGTH: 46
<212> TYPE: PRT
<213> ORGANISM: Haliotis discus

<400> SEQUENCE: 15

Ala Ala Thr Lys Pro Lys Lys Ala Gly Ala Glu Ala Ala Pro Lys Lys
1               5                   10                  15

Pro Ala Lys Lys Gln Thr Lys Lys Pro Ala Lys Lys Ala Gly Gly
                20                  25                  30

Lys Lys Lys Pro Lys Arg Ala Gly Ala Lys Lys Ala Lys Lys
            35                  40                  45

<210> SEQ ID NO 16
<211> LENGTH: 55
<212> TYPE: PRT
<213> ORGANISM: Crassostrea gigas

<400> SEQUENCE: 16

Ala Ala Thr Ala Lys Lys Gly Ala Lys Lys Ala Asp Ala Pro Ala Lys
1               5                   10                  15
```

-continued

```
Pro Lys Lys Ala Thr Lys Pro Lys Ser Pro Lys Lys Ala Ala Lys Lys
            20                  25                  30

Ala Gly Ala Lys Lys Gly Val Lys Arg Ala Gly Lys Lys Gly Ala Lys
            35                  40                  45

Lys Thr Thr Lys Ala Lys Lys
            50              55

<210> SEQ ID NO 17
<211> LENGTH: 46
<212> TYPE: PRT
<213> ORGANISM: Haliotis discus

<400> SEQUENCE: 17

Ala Ala Thr Lys Pro Lys Lys Ala Gly Ala Glu Ala Ala Pro Lys Lys
1               5                   10                  15

Pro Ala Lys Lys Gln Thr Lys Lys Lys Pro Ala Lys Lys Ala Gly Gly
            20                  25                  30

Lys Lys Lys Pro Lys Arg Ala Gly Ala Lys Lys Ala Lys Lys
            35                  40                  45
```